(12) United States Patent
von Hollen

(10) Patent No.: US 11,975,141 B2
(45) Date of Patent: May 7, 2024

(54) BREATH ACTUATED INHALERS

(71) Applicant: KONINKLIJKE PHILIPS N.V., Eindhoven (NL)

(72) Inventor: Dirk Ernest von Hollen, Somerset, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 516 days.

(21) Appl. No.: 17/285,552

(22) PCT Filed: Dec. 17, 2019

(86) PCT No.: PCT/EP2019/085538
§ 371 (c)(1),
(2) Date: Apr. 15, 2021

(87) PCT Pub. No.: WO2020/127190
PCT Pub. Date: Jun. 25, 2020

(65) Prior Publication Data
US 2021/0402115 A1 Dec. 30, 2021

Related U.S. Application Data

(60) Provisional application No. 62/781,063, filed on Dec. 18, 2018.

(30) Foreign Application Priority Data

Feb. 7, 2019 (EP) ..................................... 19156040

(51) Int. Cl.
*A61M 15/00* (2006.01)
(52) U.S. Cl.
CPC .... *A61M 15/0091* (2013.01); *A61M 15/0086* (2013.01); *A61M 15/0088* (2014.02)

(58) Field of Classification Search
CPC ........... A61M 15/0086–0088; A61M 15/0091; A61M 15/00; A61M 15/009
(Continued)

(56) References Cited

U.S. PATENT DOCUMENTS

| 5,133,343 A | 7/1992 | Johnson |
| 5,324,290 A | 6/1994 | Zdeblick |

(Continued)

FOREIGN PATENT DOCUMENTS

| CN | 201012211 | 1/2008 |
| CN | 201012211 Y | 1/2008 |

(Continued)

*Primary Examiner* — Elliot S Ruddie
(74) *Attorney, Agent, or Firm* — Daniel H. Brean

(57) ABSTRACT

An accessory (50,80) adapted to be used with a breath actuated inhaler (10), the breath actuated inhaler (10) comprising an air inlet (19), an outlet (20) for delivering medicament and a trigger mechanism (30) for triggering the delivery of a dose of the medicament in response to a flow (40) between the air inlet (19) and the outlet (20), wherein the accessory comprises: a pressure assist unit (52, 54) for application to the air inlet, comprising an assist chamber (52) for holding a volume of air and a mechanical release system (54, 70) for expelling air from the assist chamber to the air inlet, at a rate sufficient to trigger the trigger mechanism. Hence, it has an assist chamber for holding a volume of air and a mechanical release system for expelling air from the assist chamber to the air inlet, at a rate sufficient to trigger a dose trigger mechanism of the breath actuated inhaler. In this way, a user may use a breath actuated inhaler even if they do not have the ability to generate an inhalation suitable for activating the inhaler.

15 Claims, 7 Drawing Sheets

(58) Field of Classification Search
USPC .................................... 128/200.21, 200.22
See application file for complete search history.

(56) References Cited

U.S. PATENT DOCUMENTS

| | | | |
|---|---|---|---|
| 5,447,150 A * | 9/1995 | Bacon | ............... A61M 15/0096 |
| | | | 128/200.14 |
| 5,826,571 A | 10/1998 | Casper | |
| 6,286,506 B1 | 9/2001 | Berg | |
| 6,328,035 B1 | 12/2001 | Genova | |
| 6,637,432 B2 | 10/2003 | Genova | |
| 7,093,594 B2 * | 8/2006 | Harrison | ........... A61M 15/0076 |
| | | | 128/200.14 |
| 8,297,778 B2 | 10/2012 | Jeffrey | |
| 8,770,188 B2 * | 7/2014 | Stenzler | ............... A61M 15/002 |
| | | | 128/200.22 |
| 11,865,249 B2 * | 1/2024 | Petit | .................... A61M 15/009 |
| 2007/0240712 A1 | 10/2007 | Fleming | |
| 2012/0266878 A1 | 10/2012 | Canon | |
| 2015/0020798 A1 | 1/2015 | Elgaard | |
| 2018/0056022 A1 | 3/2018 | Gu | |
| 2019/0001085 A1 | 1/2019 | Cottenden | |
| 2019/0134322 A1 * | 5/2019 | Fabien | ................ A61M 15/009 |
| 2020/0069897 A1 | 3/2020 | Hodson | |
| 2021/0187210 A1 * | 6/2021 | Brouet | ................ A61M 15/009 |

FOREIGN PATENT DOCUMENTS

| | | |
|---|---|---|
| CN | 101489612 A | 7/2009 |
| EP | 0774986 B1 | 5/1997 |
| WO | 9405360 A1 | 3/1994 |

* cited by examiner

BREATH ACTUATED INHALERS

CROSS-REFERENCE TO PRIOR APPLICATIONS

This application claims the priority benefit under 35 U.S.C. § 371 of International Patent Application No. PCT/EP2019/085538, filed on Dec. 17, 2019, which claims the priority benefit of U.S. Provisional Patent Application No. 62/781,063, filed on Dec. 18, 2018 and European Patent Application No. 19156040.8, filed on Feb. 7, 2019, the contents of which are herein incorporated by reference.

FIELD OF THE INVENTION

This invention relates to breath actuated inhalers.

BACKGROUND OF THE INVENTION

For the intake of medication for obstructive airways diseases, such as chronic obstructive pulmonary disease (COPD), cystic fibrosis (CF) and asthma, inhalers are well known. There are different types of inhaler, and each type has its own advantages and disadvantages.

For example, a standard pressurized meter dose inhaler (pMDI) makes use of a canister which is depressed by the user or caregiver to release a medication dose directly to the user, with the option of using a holding chamber with an output valve, to store temporarily the delivered dose.

Inhaler technology continues to evolve to address user needs. New built-in mechanisms have been developed that allow inhalers to be automatically actuated to dispense a medication when a sufficient flow rate has been achieved based on inhalation by the user. Breath actuated (or activated) inhalers (BAIs) rely on an airflow created by the user's inhalation in order to trigger the delivery of a dose of medication. This requires a user to generate a sufficient airflow to trigger the device, as well as to be able to inhale the medication with a single breath intake.

Breath actuation has for example been deployed for dry powder inhalers (DPIs). A typical operation of a DPI involves the user achieving a required flow to collect the dose and using air turbulence to break apart the particles, as a DPI is not pressurized. The intake of a DPI dose is entirely reliant on the user's breathing effort.

Breath actuation has also been employed for a pressurized meter dose inhaler (pMDI). In this system, a predetermined flow rate activates a trigger mechanism to allow a valve to open and the contents of a pMDI dose is then dispensed under pressure.

For a certain population segment, it is difficult to coordinate the actuation of the inhaler with a single inhalation breath by the user, to allow the medication to deposit in the airways. Accessories for inhalers such as holding chambers have been developed to allow a user to breathe in the dose normally via tidal breathing which may involve single or multiple breaths.

As explained above, BAIs require a minimum constant air flow or breathing maneuverer to dispense the medication dose, which is therefore dependent on the user inhalation effort. It has also been proposed to use electronic triggers to coordinate the action or release of a dose of medication. The breath may for example be used to trigger a valve, or else breath may be detected based on flow sensing, for example using a hot wire anemometer.

As BAIs require the inhalation of a user to function, this excludes the use of this type of inhaler to a certain user population (pediatrics and seniors). Unfortunately, BAIs are not suitable for users who have difficultly achieving a flow sufficient to activate the trigger (whether mechanical or electronic), or individuals who depend on the use of a so-called valved holding chamber (VHC) (with or without mask) that allows them to inhale the dose over several breaths.

It is known to provide a dry powder inhaler with a hand-actuation system to provide a burst of air, as disclosed in US2018/0056022. The air is used to activate a piercing mechanism in order to provide a dose into a turbulent air stream for inhalation by the user.

However, there remains a need for a BAI design which enables delivery of a dose without using a user's inhalation effort. It would be desirable to achieve this aim without a redesign of the inhaler functionality, and thus still rely on a flow-based triggering of the medication delivery.

SUMMARY OF THE INVENTION

The invention is defined by the claims.

According to examples in accordance with an aspect of the invention, there is provided an accessory for use with a breath actuated inhaler, the breath actuated inhaler comprising an air inlet, an outlet for delivering medicament and a trigger mechanism for triggering the delivery of a dose of the medicament in response to a flow between the air inlet and the outlet, wherein the accessory comprises:

a pressure assist unit for application to the air inlet, comprising an assist chamber for holding a volume of air and a mechanical release system for expelling air from the assist chamber to the air inlet, at a rate sufficient to trigger the trigger mechanism.

By using a mechanical release system associated with an assist chamber, a required flow to trigger the breath actuated inhaler is ensured. In particular, a consistent flow rate can be achieved by a user with a manual action. In this way, a breath actuated inhaler does not need to be modified, in order for a user to be able to trigger a dose delivery despite being unable to generate the required flow based on their own inhalation.

The pressure assist unit is preferably adapted to allow a flow through or around the pressure assist unit to the air inlet when in a non-released configuration. In this way, a user with suitable breathing ability may use the breath actuated inhaler in a normal way, without triggering the mechanical release system. Instead, by inhaling from the outlet, a flow is generated through or around the pressure assist unit to trigger the delivery of a dose, but the assist function does not need to be used.

The mechanical release system is for example adapted to be mechanically reset. Thus, for each dose, the mechanical release system is reset so that the same air flow can be generated reliably for the next dose. This air flow depends on the volume of the assist chamber, and the extent to which that volume is expelled when triggered by the mechanical release system.

The accessory preferably further comprises a capture system for application to the outlet for capturing a delivered dose of medicament.

This capture system means the user does not need to inhale at the same time as activating the mechanical release mechanism. Instead, the delivered dose is stored in a capture system. The user may then intake that dose over multiple breaths, making the operation of the system easier for the user.

In one example, the capture system comprises a conduit.

In a preferred example, the capture system comprises a holding chamber.

The holding chamber for example comprises an input for application to the outlet of the pressurized metered dose inhaler, an output for delivering medicament to a user, and a one-way valve in series with the output. The one-way valve allows the content of the holding chamber to be breathed in by the over multiple inhalation cycles.

A face mask may for example be coupled to the output.

The assist chamber preferably has a first volume and the holding chamber has a second, greater, volume.

This arrangement limits a loss of medication through the one-way valve in series with the output of the holding chamber. In particular, if the air expelled from the assist chamber has a volume greater than the internal space of the holding chamber, part of the dose will be lost through the one-way valve, thereby decreasing the available dose to the user for inhalation.

The holding chamber may comprise a pressure relief component. It relieves excess pressure in the holding chamber when a pressurized dose is dispensed into the holding chamber, together with the volume expelled from the assist chamber.

In particular, the one-way valve at the output of the holding chamber remains closed, because the pressure relief component maintains the pressure below the level at which the one-way valve opens. Thus, the one-way valve is only opened by the negative pressure of the inhalation of the user (on the side of the one-way valve opposite to the holding chamber).

The pressure relief component can thus function as an indicator to indicate that sufficient volume has been delivered to the holding chamber. The pressure relief component is for example sensitive to flow and produces an audible sound, so that it can act also as an indicator that sufficient volume has been dispensed from the assist chamber. A small amount of excess pressure will be dissipated through the pressure relief component to assist in preventing the dose leaving through the one-way valve at the output of the holding chamber. This aids a user to know that the delivery of medication to the holding chamber has been successfully completed.

The pressure relief component may also provide a flow alert. The flow alert is a second function, which is used to inform a user that the inhalation flow is too fast.

The assist chamber may comprise a bellows having a one-way valve, wherein the mechanical release system comprises a compressed spring, which is adapted, when released, to compress the bellows thereby to expel air from the assist chamber.

The use of a mechanical spring assist type mechanism with bellows ensures a consistent flow rate with a define volume of air. For example, squeezing a bulb manually may not generate a sufficient flow rate to trigger as it is dependent on the force achieved in the action of squeezing.

The one-way valve of the assist chamber is for example adapted to allow flow through the accessory to the air inlet. As mentioned above, this enables the inhaler to be used as a normal breath actuated inhaler.

The invention also provides an inhaler system, comprising:
a breath actuated inhaler comprising an air inlet, an outlet for delivering medicament and a trigger mechanism for triggering the delivery of a dose of the medicament in response to a flow between the air inlet and the outlet; and
an accessory as defined above.

The accessory comprises at least the assist chamber, but preferably also includes the capture system so that the user can store the medication dose to allow it to be inhaled over multiple breaths.

The breath actuated inhaler is a for example a metered dose inhaler, such as a pressurized metered dose inhaler.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
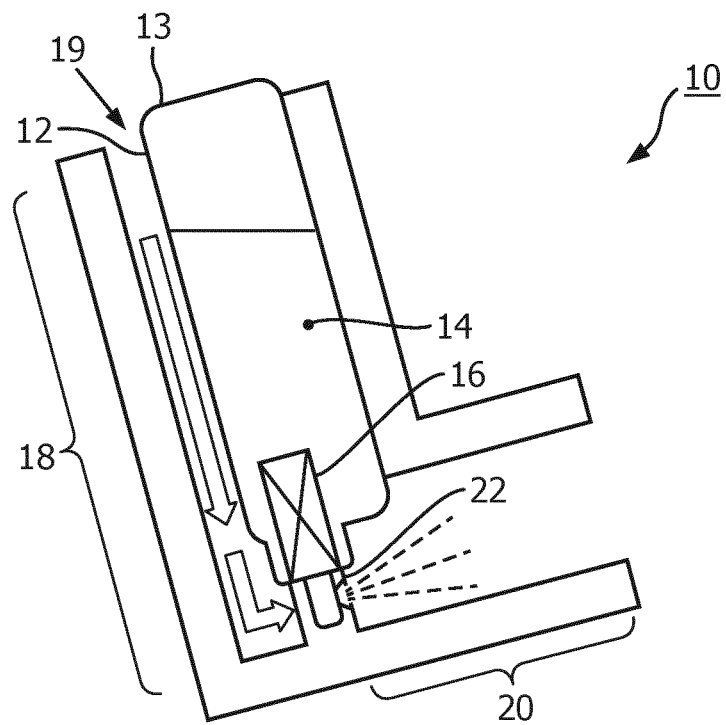
FIG. 1 shows in schematic form a conventional pressurized metered dose inhaler (pMDI)

The invention will be described with reference to the Figures. It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an accessory for application to the air inlet of a breath actuated inhaler. It has an assist chamber for holding a volume of air and a mechanical release system for expelling air from the assist chamber to the air inlet, at a rate sufficient to trigger a dose trigger mechanism of the breath actuated inhaler. In this way, a user may use a breath actuated inhaler even if they do not have the ability to generate an inhalation suitable for activating the inhaler.

FIG. 1 shows in schematic form a conventional pressurized metered dose inhaler (pMDI) 10 comprising a canister 12 containing a medicament formulation 14. The canister 12 comprises a can having a base 13 and metering valve 16 at its outlet, at the opposite end to the base. The canister 12 sits within a housing having a first tubular portion 18 having an open end dimensioned to receive the canister 12 a second tubular portion 20 in the form of a mouthpiece that defines an inspiration orifice. The open upper end of the first tubular portion 18 defines an aspiration orifice, or an air inlet 19.

A spray orifice 22 delivers a metered dose of medication when the inhaler is actuated.

In use, a user places the mouthpiece 20 into their mouth and then inhales through it while at the same time pressing downwards on the base 13 of the canister 12. The pressing force serves to move the canister 12 downwards and this movement isolates a metered dose of medicament formulation from the medication formulation 14 in the canister and then discharges the dose.

This design requires good user coordination between the timing of the start of inhalation and the moment at which the canister 12 is pressed downwards.

Full details of the design of the inhaler are not shown, as various options will be well known to those skilled in the art.

It is known to provide breath actuation, whereby the dose of medication is delivered based on detection of a flow generated by the inhalation of the user.

Figure 2:
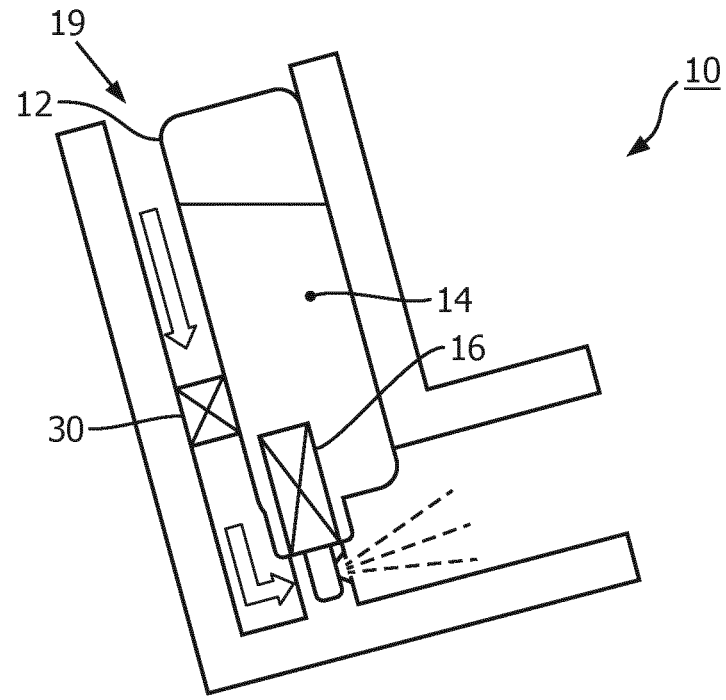
FIG. 2 shows in schematic form a known modification to the design of FIG. 1 to provide breath actuation.

FIG. 2 shows in schematic form a known modification to the design of FIG. 1 to provide breath actuation. A valve 30 is provided which opens in response to a flow of air generated by inhalation at the mouthpiece 20. Movement of the valve is detected as way of detecting the flow, for example based on the valve movement physically operating a switch, and the dose release is then controlled automatically in response to this flow detection.

The valve 30 has a threshold such that it will only open when a sufficient breath flow is created, to prevent accidental actuation. This means that the user requires a certain breathing ability to be able to use the breath actuated inhaler.

Figure 3:
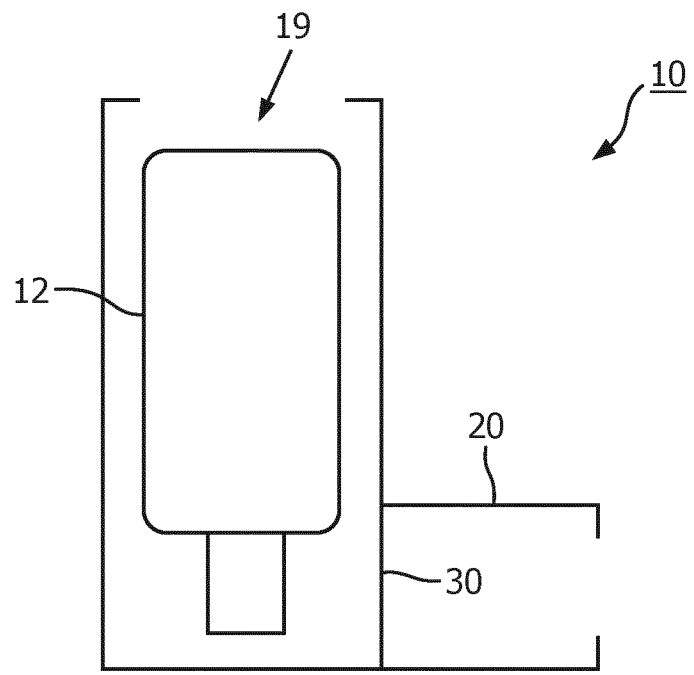
FIG. 3 shows a simplified representation of the breath actuated inhaler for use in subsequent figures.

To explain the system of the invention, the breath actuated inhaler will be represented in simplified form as shown in FIG. 3. The valve 30 is shown in simplified form as a flap valve which opens to generate a dose and allow it to flow to the mouthpiece 20.

Figure 4:
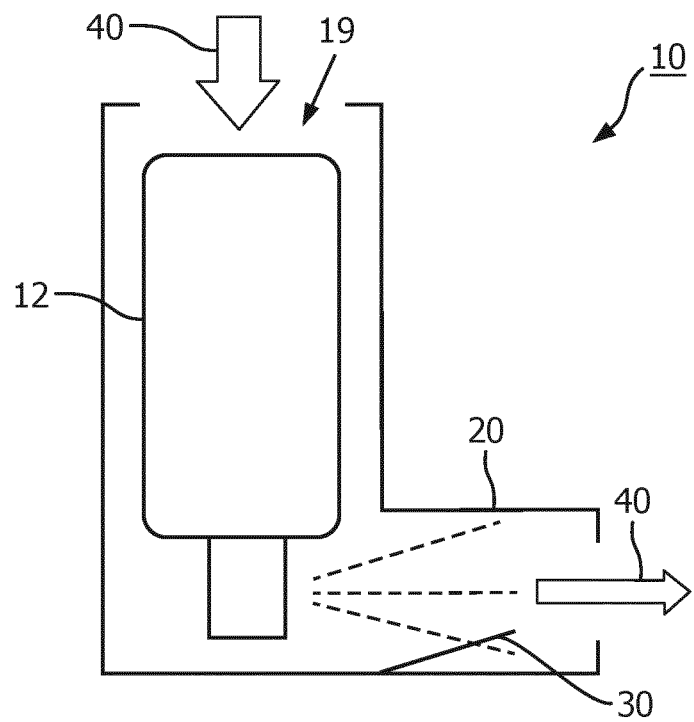
FIG. 4 shows the conventional use of the breath actuated inhaler of FIG. 3.

FIG. 4 shows the conventional use of the breath actuated inhaler of FIG. 3. The user inhales through the mouthpiece 20. The resulting flows is shown by arrows 40. The flow opens the valve 30 and is detected so as to cause the metered dose to be delivered.

Figure 5:
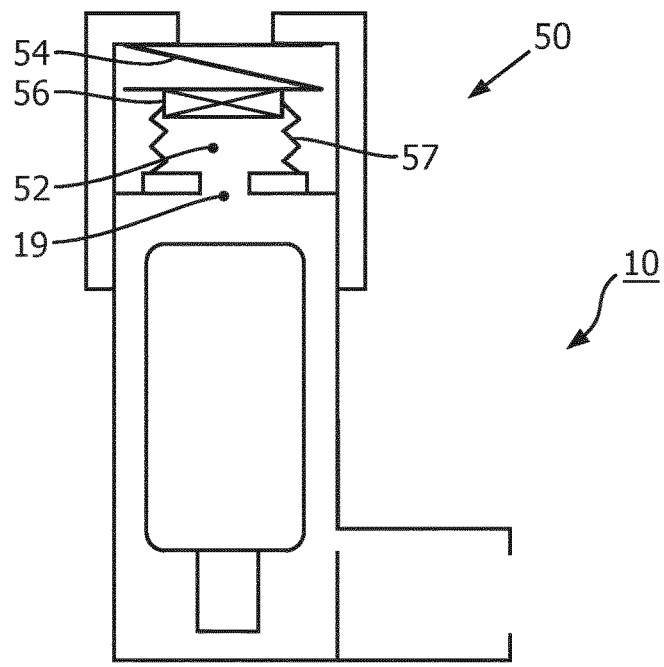
FIG. 5 shows the modification to the inhaler of FIG. 2 in accordance with one example of the invention.

FIG. 5 shows the modification in accordance with one example of the invention.

The invention provides an accessory 50 mounted over the air inlet 19 at the upper end of the housing. It comprises an assist chamber 52 for holding a volume of air and a mechanical release system, in this example in the form of a compressed spring 54, for expelling air from the assist chamber 52 to the air inlet 19, at a rate sufficient to trigger the trigger mechanism of the breath actuated inhaler. The assist chamber 52 and spring 54 may together be considered to constitute a pressure assist unit.

The assist chamber 52 comprises a bellows 57 and a one-way valve 56. The spring 54 is adapted, when released, to compress the bellows 57 thereby to expel air from the assist chamber.

In the example shown, the one-way valve 56 defines a top of the chamber 52 and the bottom is open. The spring 54 is held in a compressed state, and when released, for example by a user actuating a release trigger, compresses the bellows so that the air in the assist chamber 52 is driven through the air inlet 19. This creates a flow sufficient to open the valve 30 and thereby trigger the delivery of a medication dose.

The use of a mechanical spring mechanism with a bellows ensures a consistent flow rate with a defined volume of air. The volume of the assist chamber 52 and the flow rate (dependent on the force applied by the compressed spring 54) are designed to enable the opening of the valve 30.

The one-way valve 56 allows flow through the accessory to the air inlet.

Figure 6:
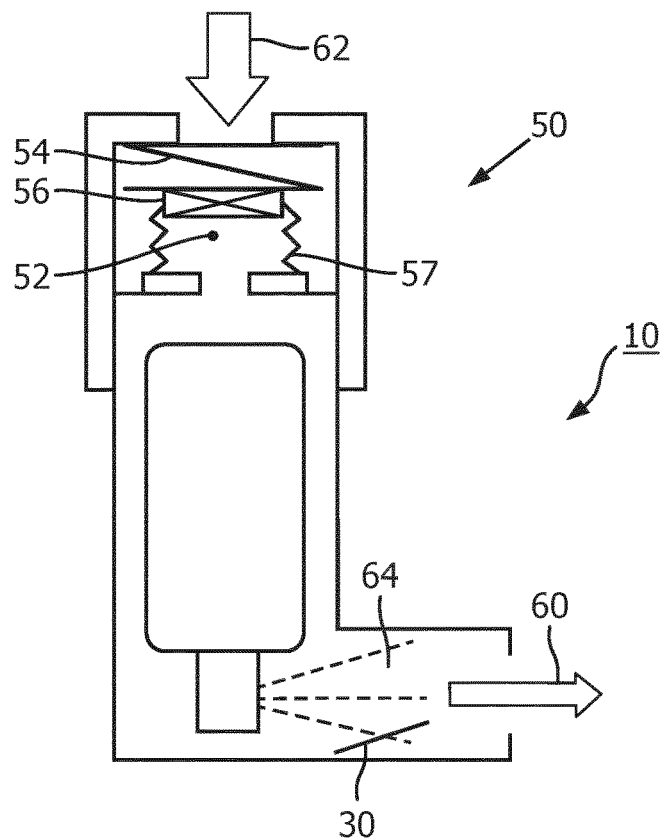
FIG. 6 shows use of the inhaler of FIG. 5 as a normal breath actuated inhaler.

This enables the inhaler to be used as a normal breath actuated inhaler. This use of the inhaler is shown in FIG. 6.

An inhalation 60 by the user draws an air flow 62 through the accessory 50, in particular through the one-way valve 56 even though the assist chamber remains non-activated with its full volume. The valve 30 is opened by the air flow, and this air flow thus triggers the delivery of a dose 64. Thus, the breath actuated inhaler may be used in conventional manner.

Figure 7:
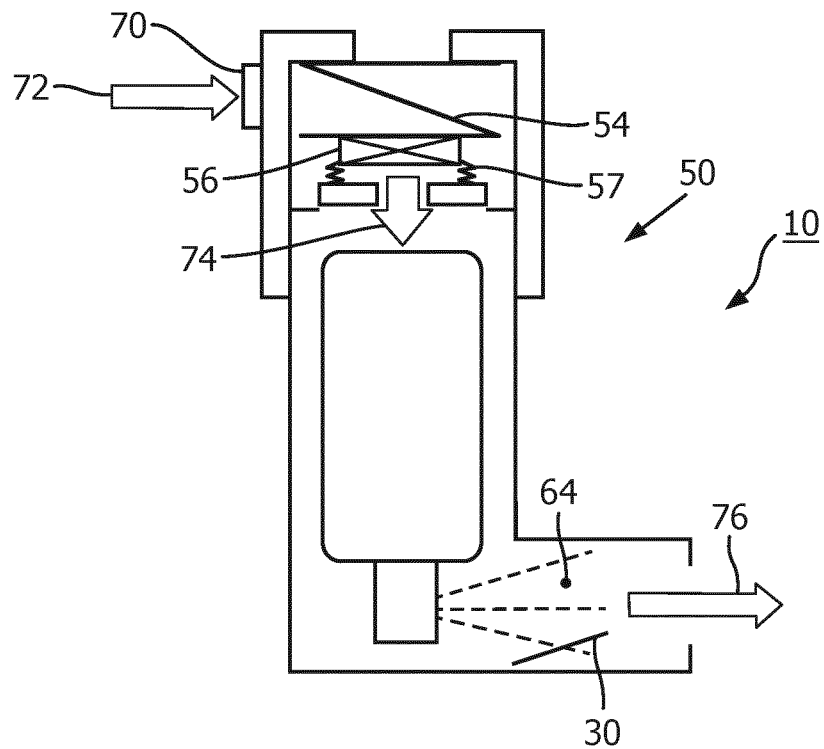
FIG. 7 shows how delivery of a dose of medication is triggered by the accessory of the inhaler of FIG. 5.

FIG. 7 shows how delivery of a dose of medication is triggered by the accessory 50. By releasing the spring 54, for example by actuating a trigger 70 as represented by arrow 72, the spring 54 expands, and thereby compresses the bellows to cause the volume of the assist chamber (or more accurately the change in volume) to be delivered to the air inlet 19, as shown by arrow 74. The resulting volume and flow rate of air is sufficient to open the valve 30 and trigger the delivery of a dose 64 as represented by arrow 76.

The trigger for example comprises a latch. When the spring 54 is compressed to store energy, it toggles a latch which holds the spring in its compressed state. The user simply needs to activate the latch (i.e. release the spring from its compressed state), for example by pushing on the trigger 70, to release the spring.

In theory, the dose may then be inhaled directly by the user. In this case, the invention enables a breath actuated inhaler to be used in the manner of a conventional pressurized metered dose inhaler. The pushing of the canister explained with reference to FIG. 1 is replaced by a release of a spring loaded mechanism. This may be easier for the user, and it enables a breath actuated inhaler to be used either as a breath actuated device or as a mechanically actuated device.

However, a preferred use of the inhaler, when breath actuation is not possible for the user, is to provide a capture system at the mouthpiece, for capturing a delivered dose of medicament.

This capture system means the user does not need to inhale at the same time as activating the mechanical release mechanism. Instead, the delivered dose is stored in the capture system. The user may then intake that dose over multiple breaths, making the operation of the system easier for the user.

The capture system may simply comprise a conduit. However, a preferred example shown in FIG. 8 makes use of a capture system in the form of a holding chamber 80.

The holding chamber 80 comprises an input 82 for application to the mouthpiece 20 of the pressurized metered dose inhaler, an output 84 for delivering medicament to a user, and a one-way valve 86 in series with the output. The one-way valve 86 allows the content of the holding chamber to be breathed in by the user over multiple inhalation cycles. The output 84 may for example lead to a face mask 88.

The assist chamber 52 has a first maximum volume V1 and the holding chamber 80 has a second volume V2, where V2>V1. This arrangement limits loss of medication through the one-way valve 86 at the output of the holding chamber.

In particular, when the air is released from the assist chamber 52, and enters the holding chamber 80, carrying with it the medication dose, displaced air which leaves the holding chamber 80 will comprise the clean air previously in the holding chamber, so that part of the medication dose is not lost through the one-way valve 86.

When the air from the assist chamber 52 is expelled towards the holding chamber 80, there will be an increase in pressure. Depending on the threshold for the one-way valve 86, this pressure may remain elevated until a user inhales through the face mask 88, or else part of the pressure may be released by the valve 86.

Figure 8:
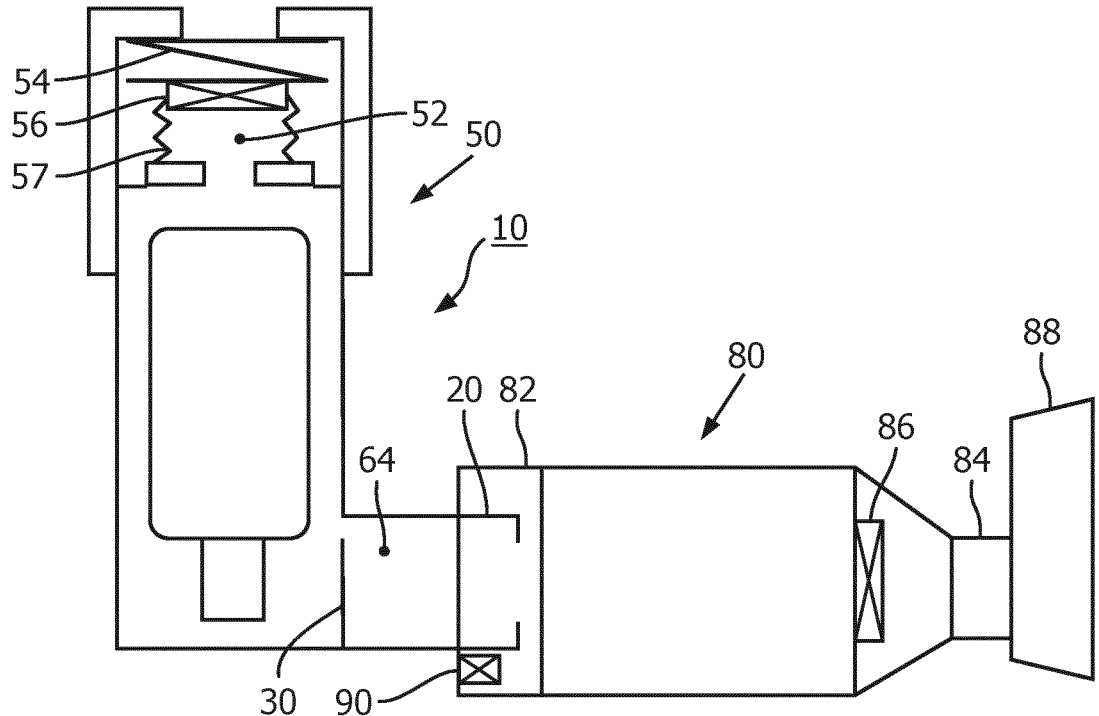
FIG. 8 shows the additional use of a capture system in the form of a holding chamber.

FIG. 8 shows an additional pressure relief component 90. This may be used instead to relieve excess pressure in the holding chamber when a pressurized dose is dispensed into the holding chamber, together with the volume expelled from the assist chamber.

The pressure relief component is positioned out of the path of the medication dose, so that the pressure relief function is less likely to cause the release of part of the medication dose. For example, the pressure relief component is mounted at the end of the holding chamber 80 which connects to the inhaler and hence the opposite end to the one-way valve 86, as shown.

In particular, the one-way valve 86 at the output of the holding chamber may remain closed during pressure relief through the component 90, because the pressure relief component 90 maintains the pressure in the holding chamber 80 below the level at which the one-way valve 86 opens.

Figure 9:
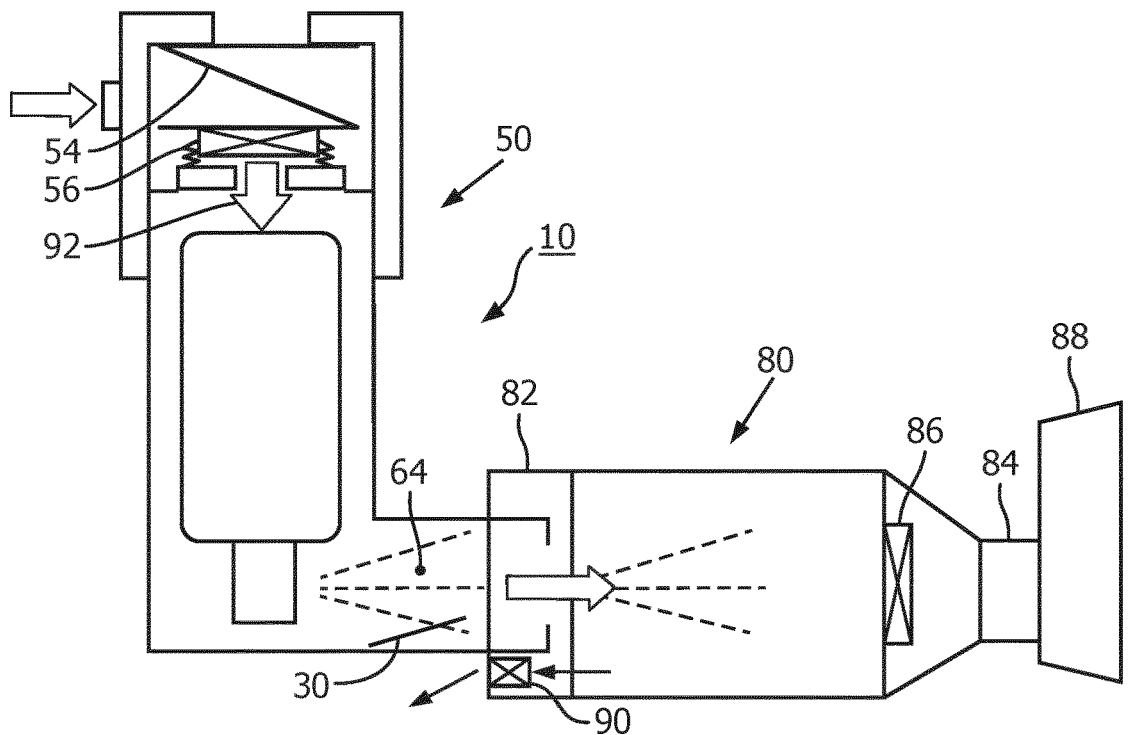
FIG. 9 shows the flows in the inhaler system of FIG. 8 when the release mechanism is triggered.

FIG. 9 shows the flows in the inhaler system when the release mechanism is triggered. The spring 54 expands (and the bellows thereby compresses) causing a flow 92 to actuate the trigger mechanism of the inhaler, thus causing a dose 64 to be delivered to the holding chamber 80. Some medication will also reside in the internal volume of the inhaler.

Note that the valve 30 is only a schematic representation of any possible trigger mechanism, which is part of the inhaler to which the accessory 50 is connected.

The pressure relief component 90 prevents buildup of pressure in the holding chamber 80 and thereby maintains the one-way valve 86 closed. However, it is out of the path of the delivered medication dose so does not cause loss of medication.

The pressure relief component 90 may simply comprise an opening or hole. This opening can then function as a sound reed to give a whistle indication when there is sufficient flow through the opening. In this way the pressure relief component 90 may provide an audible tone to inform the user that the delivery of medication to the holding chamber has taken place. When the assist chamber forces a volume into the holding chamber some of the flow will escape through the pressure relief component in the opposite direction of inhalation flow creating the momentary audible sound.

The pressure relief component may instead comprise a passive valve which opens and closes in response to a pressure difference. A pMDI allows flow both ways through the inhaler so there is little or no pressure build up to control a valve function. However, a low resistance one-way valve may be used as this will ensure that drug is not lost. The sound reed function is for example activated by a flow rate in the region of 5 to 10 liters per minute.

Figure 10:
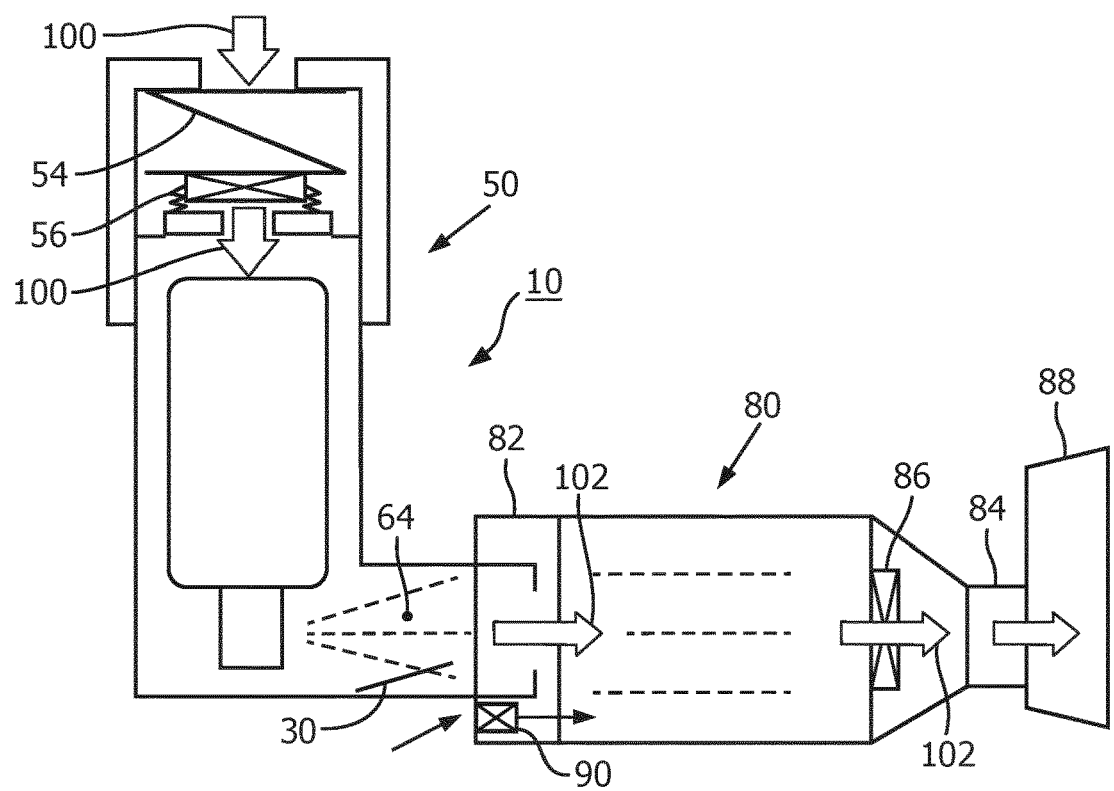
FIG. 10 shows the user inhaling the medication previously in the holding chamber in FIG. 9.

FIG. 10 shows the user inhaling the medication previously in the holding chamber. By applying a negative pressure, i.e. inhalation, to the face mask 88, the one-way valve 86 is opened, and the contents of the holding chamber 80 can be inhaled. During this time, there is an air flow 100 through the accessory as well as the air flow 102 through the holding chamber. Thus any medication in the internal volume of the inhaler is also drawn out through the holding chamber 80. The user may take the dose of medication over the course of multiple breaths.

The pressure relief component 90 in this phase may also provide a flow alert. The flow alert is used to inform a user that the inhalation flow is too fast. In particular, breathing in too fast or hard results in drug impacting the back of the patient's throat and thus preventing it to reach the lung.

The mechanical release system is mechanically reset. Thus, for each dose, the mechanical release system is reset so that the same air flow can be generated reliably for the next dose.

Figure 11:
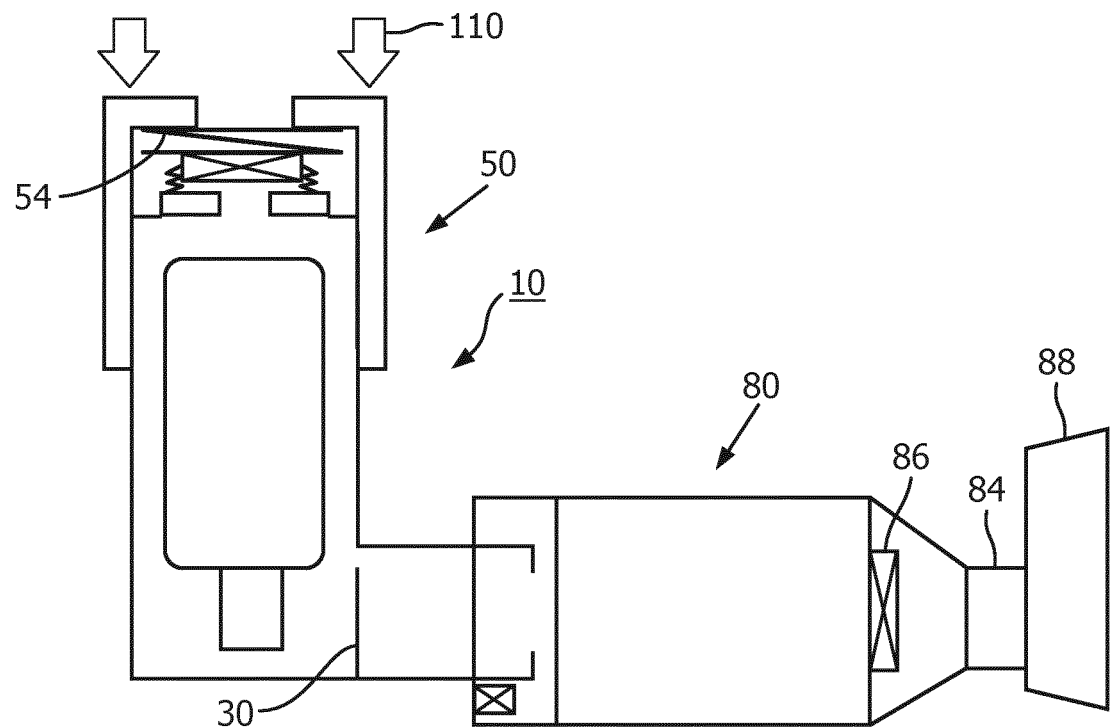
FIG. 11 shows how the accessory is mechanically reset.

FIG. 11 shows the mechanical reset. The accessory 50 is pushed down to re-compress the spring 54. It is then retained in its compressed state by a latch or any other suitable catch arrangement. The accessory is then lifted back to its original position with the spring held in its compressed state. The bellows may provide some assistance for it to return to its expanded state.

Figure 12:
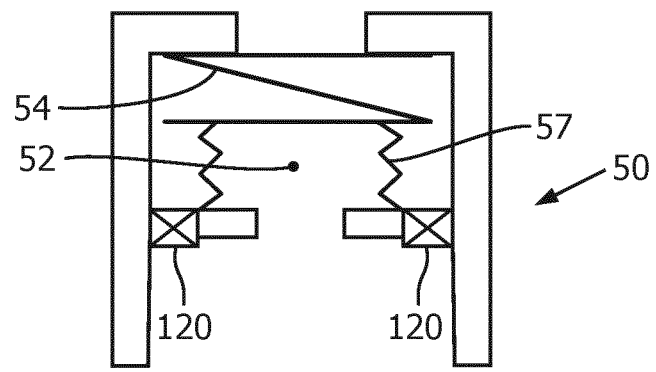
FIG. 12 shows an alternative design of the accessory.

In the example above, the accessory has a one-way valve 56 in series with the assist chamber. However, as shown in FIG. 12, the one-way valve 120 may instead be in parallel, so that a flow can pass around the cavity 52 rather than through it, when the accessory is not used, namely when the system is being used as a normal breath actuated system.

The example above makes use of a bellows, but a piston arrangement may instead be used. Thus, any latched system which can deliver a controlled burst of air when released may be used.

Figure 13:
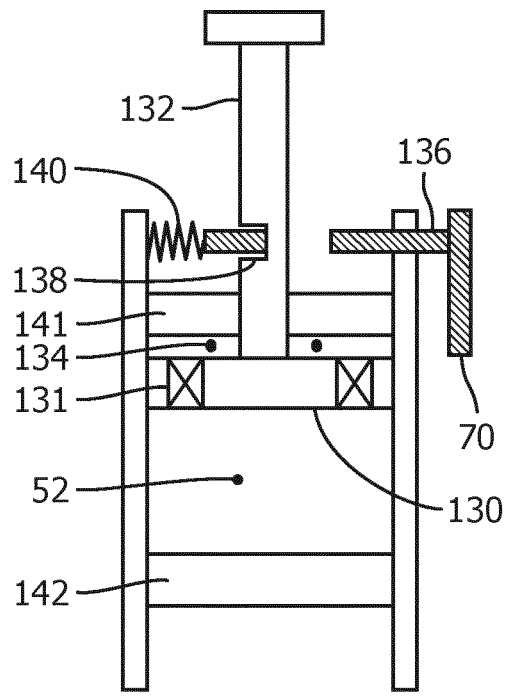
FIG. 13 shows another design of the accessory in a set to fire configuration.
Figure 14:
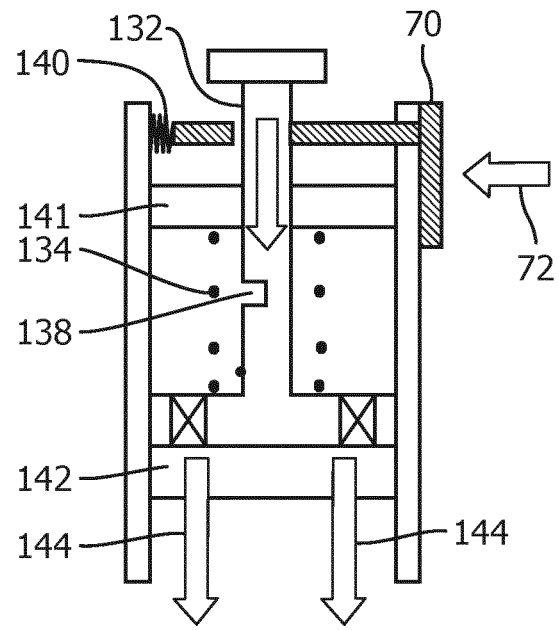
FIG. 14 shows the design of FIG. 13 after firing.
Figure 15:
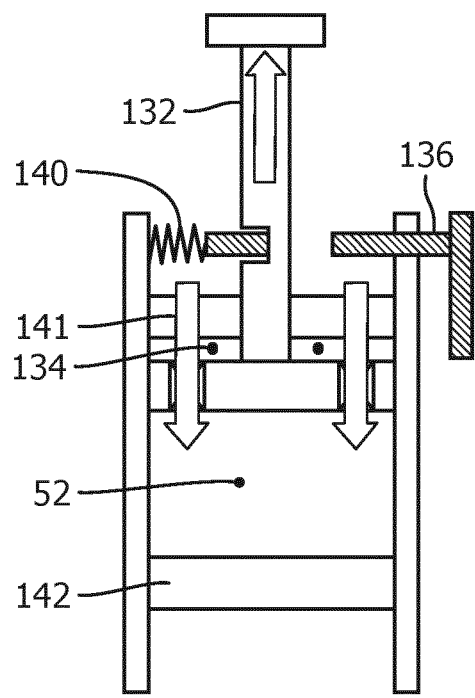
FIG. 15 shows the resetting of the device of FIG. 13.

FIGS. 13 to 15 shows a piston arrangement.

FIG. 13 shows the piston arrangement in a set to fire configuration. A piston 130 has a control shaft 132. A spring 134 (equivalent to the spring 54 in the examples above) is in a compressed state and it is held in this state by a latch 136 which engages with a notch 138 in the control shaft 132. The latch is held in this set to fire state by a spring 140 (or other resilient/compressible member). This causes a fire trigger 70 to project outwardly.

A top layer 141 above the piston 130 provides a seat for the spring 134. It allows air to fill the space behind the piston when it is fired. A one-way valve 131 is incorporated in piston.

FIG. 14 shows the arrangement after firing. To fire the device, the trigger 70 is pushed (as shown by arrow 72). This releases the latch 136 from the notch 138 so the piston (and shaft) are driven down by the spring 134. The air in the assist chamber 52 is thus driven into the inhaler beneath (not shown), through the open top 142 of the inhaler, as represented by arrows 144. Air is able to fill the space behind the piston 130 during piston movement through the top layer 141.

FIG. 15 shows the resetting operation. The piston is pulled up, compressing the spring 134 until it is latched in the set to fire configuration. During this time, air can flow into the assist cavity 52 through the one-way valve 131 in the piston 130 (and through the top layer 141).

This shows a series arrangement but a parallel arrangement is also possible as shown for a bellows design in FIG. 12.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims. The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. An accessory adapted to be used with a breath actuated inhaler, the breath actuated inhaler comprising an air inlet, an outlet for delivering medicament and a trigger mechanism for triggering the delivery of a dose of the medicament in response to a flow between the air inlet and the outlet, wherein the accessory comprises:
   a pressure assist unit for application to the air inlet, comprising an assist chamber for holding a volume of air and a user-activated latched mechanical release system for expelling air from the assist chamber to the air inlet, at a rate sufficient to trigger the trigger mechanism.

2. An accessory as claimed in claim 1, wherein the pressure assist unit is adapted to allow a flow through or around the pressure assist unit to the air inlet when in a non-released configuration.

3. An accessory as claimed in claim 1, wherein the mechanical release system is adapted to be mechanically reset.

4. An accessory as claimed in claim 1, further comprising a capture system for application to the outlet for capturing a delivered dose of medicament.

5. An accessory as claimed in claim 4, wherein the capture system comprises a conduit.

6. An accessory as claimed in claim 4, wherein the capture system comprises a holding chamber.

7. An accessory as claimed in claim 6, wherein the holding chamber comprises an input for application to the outlet of the breath actuated inhaler, an output for delivering medicament to a user, and a one-way valve in series with the output.

8. An accessory as claimed in claim 7, further comprising a face mask coupled to the output.

9. An accessory as claimed in claim 6, wherein the assist chamber has a first volume and the holding chamber has a second, greater, volume.

10. An accessory as claimed in claim 6, wherein the holding chamber comprises a pressure relief component.

11. An accessory as claimed in claim 10, wherein the pressure relief component provides a flow alert.

12. An accessory as claimed in claim 1, wherein the assist chamber comprises a bellows having a one-way valve, wherein the user-activated latched mechanical release system comprises a compressed spring, which is adapted, when released, to compress the bellows thereby to expel air from the assist chamber.

13. An accessory as claimed in claim 12, wherein the one-way outlet valve is adapted to enable flow through the accessory to the air inlet.

14. An inhaler system, comprising:
   a breath actuated inhaler comprising an air inlet, an outlet for delivering medicament and a trigger mechanism for triggering the delivery of a dose of the medicament in response to a flow between the air inlet and the outlet; and
   an accessory as claimed in claim 1.

15. An inhaler system as claimed in claim 14, wherein the breath actuated inhaler is a metered dose inhaler.

* * * * *